United States Patent [19]
Tessman et al.

[11] Patent Number: 5,532,145
[45] Date of Patent: Jul. 2, 1996

[54] METHODS FOR TREATMENT OF ENZYME PREPARATIONS

[75] Inventors: John W. Tessman, San Leandro; George D. Cimino, Richmond; Stephen T. Isaacs, Orinda; John E. Hearst, Berkeley, all of Calif.

[73] Assignee: Steritech, Inc., Concord, Calif.

[21] Appl. No.: 979,789

[22] Filed: Nov. 20, 1992

Related U.S. Application Data

[63] Continuation-in-part of Ser. No. 428,494, Oct. 26, 1989, Pat. No. 5,221,608.
[51] Int. Cl.$^6$ .............................. C12P 19/34; C12Q 1/68; C07H 21/04
[52] U.S. Cl. .............................. 435/91.2; 435/6; 435/810; 536/22.1; 536/23.1; 536/24.1; 536/24.33; 935/77; 935/78; 935/88
[58] Field of Search .............................. 435/6, 91, 810, 435/91.2; 536/24.33, 22.1, 23.1, 24.1; 935/77, 78, 88

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,196,281 | 4/1980 | Hearst et al. | 536/28 |
| 4,683,195 | 7/1987 | Mullis et al. | 435/6 |
| 4,683,202 | 7/1987 | Mullis et al. | 435/91 |
| 4,727,027 | 2/1988 | Wiesehahn et al. | 435/173 |
| 4,748,120 | 5/1988 | Wiesehahn | 435/173 |
| 4,889,818 | 10/1989 | Gelfand et al. | 435/194 |
| 5,139,940 | 8/1992 | Isaacs et al. | 435/91 |

OTHER PUBLICATIONS

Brown et al. (1982) Gene, vol. 20, pp. 139–144.
G. D. Cimino et al., "Psoralens as Photoactive Probes of Nucleic Acid Structure and Function: Organic Chemistry, Photochemistry, and Biochemistry," Ann. Rev. Biochem. 54:1151 (1985).

Kaledin et al., "Isolation and Properties of DNA Polymerase From Extremely Thermophilic Bacterium *Thermus aquaticus* YT1," Biokhymiya 45:644–651 (1980).
A. Chien et al., "Deoxyribonucleic Acid Polymerase from the Extreme Thermophile *Thermus aquaticus*," J. Bacteriol. 127:1550–1557 (1976).
H. A. Rotbart, "Diagnosis of Enteroviral Meningitis with the Polymerase Chain Reaction," J. Pediatr. 117:85 (1990).
C. Y. Ou et al., "DNA Amplification for Direct Detection of HIV–1 in DNA of Peripheral Blood Mononuclear Cells," Science 39:295 (1988).
J. E. Hearst et al., "The Reaction of the Psoralens with Deoxyribonucleic Acid," Quart. Rev. Biophys. 17:1 (1984).
S. T. Isaacs et al., "Synthesis and Characterization of New Psoralen Derivatives with Superior Photoreactivity with DNA and RNA," Biochemistry 16:1058 (1977).
J. E. Hyde and J. E. Hearst, "Binding of Psoralen Derivatives to DNA and Chromatin: Influence of the Ionic Environment on Dark Binding and Photoreactivity," Biochemistry 17:1251 (1978).
J. F. Thompson et al., "Determination of the Secondary Structure of Drosophilia Melanogaster 5 S RNA by Hydroxymethyltrimethylpsoralen Crosslinking," J. Mol. Biol. 147:417 (1981).
J. F. Thompson et al., "Dependence of 4'–(Hydroxymethyl)–4,5', 8–trimethylpsoralen Photoaddition on the Conformation of Ribonucleic Acid," Biochemistry 21:1363 (1982).
A. Guiotto et al., "6–Methylangelicins: A New Series of Potential Photochemotherapeutic Agents for the Treatment of Psoriasis," J. Med. Chem. 27:959 (1984).

(List continued on next page.)

*Primary Examiner*—W. Gary Jones
*Assistant Examiner*—Ardin H. Marschel
*Attorney, Agent, or Firm*—Peter G. Carroll; Kathryn P. Wilke

[57] ABSTRACT

Method useful for solving the problem of contamination of protein with nucleic acid. Rendering amplifiable contaminating nucleic acid in enzyme preparations substantially unamplifiable prior to use of the enzyme.

7 Claims, 8 Drawing Sheets

OTHER PUBLICATIONS

I. Willis and J. M. Menter, "Psoralens: A Search for More Effective Derivatives for Photochemotherapeutic Regimens," Nat. Cancer Inst. Monograph 66 (1985).

P. D. Moore et al., "Sites of Termination of in vitro DNA Synthesis on Ultraviolet— and N—acetylaminofluorene–treated OX174 Templates by Prokaryotic and Eukaryotic DNA Polymerase," Proc. Natl. Acad. Sci. 78:110 (1981).

P. D. Moore et al., "Effect of Acetylated and Deacetylated 2–aminofluorene Adducts on in vitro DNA Synthesis," Proc. Natl. Acad. Sci. 79:7166 (1982).

J. G. Piette and P. D. Moore, "DNA Synthesis on OX174 Template Damaged by Proflavine and Light Treatment," Photochem. Photobiol. 35:705 (1982).

Y. Jinno et al., "Use of Psoralen as Extinguisher of Contaminated DNA in PCR," Nucleic Acids Research 18:6739 (1990).

T. M. Schmidt et al., "Detection of DNA Contamination in Taq Polymerase," Biotechniques 11:176 (1991).

T. J. White et al., "The Polymerase Chain Reaction: Clinical Applications," Advances in Clin. Chem. 29:161 (1992).

METHODS FOR TREATMENT OF ENZYME PREPARATIONS

This is a continuation-in-part of patent application Ser. No. 07/428,494, filed in the United States Patent and Trademark Office on Oct. 26, 1989, now U.S. Pat. No. 5,221,608, issued Jun. 22, 1993.

FIELD OF THE INVENTION

The present invention generally relates to methods for rendering nucleic acid unamplifiable.

BACKGROUND OF THE INVENTION

Advances in nucleic acid technology have made possible the manipulation, selection and characterization of a large number of eukaryotic, prokaryotic and viral genes. The application of nucleic acid amplification techniques has provided access to greater volumes of nucleic acid within relatively short periods of time, thereby speeding each of these processes.

Currently, one of the most important nucleic acid amplification techniques is the polymerase chain reaction (PCR). K. B. Mullis et al., U.S. Pat. Nos. 4,683,195 and 4,683,202, describe a method for increasing the concentration of a segment of a target sequence in a mixture of genomic DNA without cloning or purification. "Amplification" is defined as increasing the concentration of a segment of a target sequence of genomic DNA.

This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then are annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction". Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies. Thus contamination of PCR with extraneous DNA is a serious problem. Because PCR is capable of large amplification of single copies of template DNA, even minor contamination of PCR can compromise experimental results. This becomes a persistent obstacle, especially when amplifying a small sample of DNA.

One specific source of contamination in PCR is commercially prepared Taq polymerase. Contaminating nucleic acid is inherent in these commercial preparations. Contamination has been found in commercially available preparations of Taq from all vendors that offer the enzyme. The DNA contaminating Taq is evidently small in size, although there is some variation in the maximal length of product that is amplified. This presumably relates to differing degrees of contamination of different lots of the enzyme. Schmidt, et al., "Detection of DNA Contamination in Taq Polymerase," Biotechniques 11:176 (1991). The contamination of Taq polymerase imparts a significant uncertainty to the results of PCR.

Control of Contamination

The preparation of enzymes for laboratory use often requires the application of recombinant DNA techniques. Vectors containing the gene encoding the desired enzyme are inserted in host organisms. The organisms are then propagated. Finally, the desired protein is extracted. The host organisms may carry multiple vectors, representing substantial amounts of potentially contaminating nucleic acid.

At present, there is one approach for the control of contamination of enzyme preparations by the vector and host nucleic acid: better purification. Kaledin et al., Biokhymiya (1980) 45:644–651 discloses a six-step isolation and purification procedure of DNA polymerase from cells of *T. aquaticus*. These steps involve isolation of crude extract, DEAE-cellulose chromatography, fractionation on hydroxyapatite, fractionation on DEAE-cellulose, and chromatography on single-strand DNA-cellulose. A. Chien et al., J. Bacteriol. 127:1550–1557 (1976) describes a second purification scheme. In this process, the crude extract is applied to a DEAE-Sephadex column. The dialyzed pooled fractions are then subjected to treatment on a phosphocellulose column. The pooled fractions are dialyzed and bovine serum albumin is added to prevent loss of polymerase activity. The resulting mixture is loaded on a DNA-cellulose column. U.S. Pat. No. 4,889,818, to Gelfand et al., hereby incorporated by reference, describes yet another purification scheme. In this process, the crude extract is applied to a DEAE-cellulose column, followed by fractionation on hydroxyapatite, fractionation on DEAE-cellulose, and finally, the fraction is applied to a phosphocellulose column.

Ideally, purifying the amplification enzyme so that it is 100% free of DNA would eliminate from the PCR amplification any DNA inadvertently introduced in the enzyme. However, purification is never 100%; purification can only reduce, not eliminate, the contamination. Due to the sensitivity of the PCR reaction, better purification may still result in significant amplification of the contaminating nucleic acid introduced into PCR from the enzyme preparation.

There are two alternative approaches to control of contamination that are commonly used in laboratories, containment and elimination. Neither can solve the particular problem of contamination of amplification enzymes at the source manufacturer. With the containment approach, amplification is performed in a closed system, such as a designated and closed off part of the laboratory. With the elimination approach new stocks of enzymes, buffers, and other reagents are prepared along with a complete and thorough cleaning of the laboratory area where amplification is performed. Neither containment nor elimination will work here because neither will keep out contamination from reagents that are contaminated at the source manufacturer and brought into the closed system.

Accordingly, there remains a need in the art for a method of rendering nucleic acid in enzyme preparations unamplifiable that may be used to improve the PCR amplification process described above.

SUMMARY OF THE INVENTION

The present invention generally relates to methods for rendering nucleic acid in enzyme preparations unamplifiable. The resulting purified material may be used in a temperature-cycling amplification reaction, such as PCR, wherein nucleic acid sequences are produced from a given nucleic acid sequence in amounts that are large compared to the amount initially present.

One aspect of the invention provides a method for treating protein preparations, comprising a) providing in any order, one or more protein preparations suspected of containing amplifiable contaminating nucleic acid, one or more activation compounds, as reaction components; b) adding in any order, said protein preparation, said activation compound, to make a reaction mixture; and c) activating said activation compounds for the purpose of rendering said amplifiable contaminating nucleic acid unamplifiable.

In present embodiments of the invention, the amplifiable contaminating nucleic acid is DNA or RNA and the protein preparation is an enzyme, such as an amplification enzyme that is appropriate to a particular amplification system. In one embodiment, the enzyme is thermally stable polymerase, such as *Thermus aquaticus* polymerase. The present invention also contemplates that the enzyme preparation is a restriction enzyme. In one embodiment of the invention, the method further comprises removing substantially all oxygen gas from said reaction mixture before activating said activation compounds.

Another aspect of the invention provides a method for rendering nucleic acid in enzyme preparations unamplifiable, comprising a) providing in any order, one or more enzyme preparations suspected of containing amplifiable contaminating nucleic acid, one or more photoreactive activation compounds, as reaction components; b) adding in any order, said enzyme preparation, said photoreactive activation compound, to make a reaction mixture; and c) activating said photoreactive activation compounds for the purpose of rendering said amplifiable contaminating nucleic acid unamplifiable.

In one embodiment, the enzyme preparation is a thermally stable polymerase. The thermally stable polymerase may be *Thermus aquaticus* polymerase. In one embodiment, the method further comprises removing substantially all oxygen gas from said reaction mixture before activating said photoreactive activation compounds.

In another embodiment, the photoreactive activation compounds are activated by exposure of said reaction mixture to ultraviolet radiation, such as a fluorescent source of ultraviolet radiation.

The present invention contemplates activating the photoreactive activation compounds before adding them to the reaction mixture. The present invention also contemplates activating the photoreactive activation compounds after adding them to the reaction mixture.

Another aspect of the invention provides a method for rendering nucleic acid in amplification enzymes unamplifiable, comprising; a) providing in any order, one or more amplification enzymes suspected of containing amplifiable contaminating nucleic acid, one or more furocoumarin derivatives, as reaction components; b) adding in any order, said amplification enzyme, said furocoumarin derivative, to make a reaction mixture; and c) activating said furocoumarin derivative for the purpose of rendering said amplifiable contaminating nucleic acid unamplifiable.

In one embodiment, the amplification enzyme is a thermally stable polymerase. The thermally stable polymerase may be *Thermus aquaticus* polymerase. In one embodiment, the method further comprises removing substantially all oxygen gas from said reaction mixture before activating said furocoumarin derivative.

The method of the present invention is particularly useful where the furocoumarin derivative is a psoralen or an isopsoralen. In one embodiment, the photoreactive compounds are isopsoralens. In one embodiment, the isopsoralen(s) is selected from the group consisting of 5-methylisopsoralen (MIP), 5-aminomethylisopsoalen (DMIP), and their radiolabelled derivatives. In still other embodiments, the isopsoralen is selected from the group consisting of 4,5'-dimethylisopsoralen (DMIP), 4'-aminomethyl-4,5'-dimethylisopsoralen (AMDMIP), and their radiolabelled derivatives. In still other embodiments, a mixture of isopsoralens is used.

Te present invention contemplates the use of psoralens as well. In one embodiment, the linear furocoumarin 4'-aminomethyl- 4,5',8-trimethylpsoralen (AMT) is used as an agent to render the amplifiable contaminating nucleic acid substantially refractory to further amplification. In one embodiment, the photoreactive compounds are psoralens. In one embodiment, the psoralen is 4'-hydroxymethyl-4,5',8-trimethylpsoralen (HMT)

DESCRIPTION OF THE INVENTION

The present invention generally relates to methods for rendering nucleic acid in enzyme preparations unamplifiable, and in particular to methods for rendering DNA in Taq polymerase unamplifiable before the Taq polymerase is used in PCR.

The present invention contemplates a method of treatment that is useful for, among other uses, solving the problem of enzyme contamination associated with amplification of nucleic acid. The overall approach of the method involves rendering amplifiable contaminating nucleic acid substantially unamplifiable before it is introduced into PCR.

It has been found that commercial preparations of amplification enzymes are often contaminated with amplifiable nucleic acid. One specific source of contamination in PCR is commercially prepared Taq polymerase. Contaminating nucleic acid is inherent in these commercial preparations. Contamination has been found in commercially available preparations of Taq from all vendors that offer the enzyme. Schmidt, et al., supra, Biotechniques 11:176 (1991).

Without intending to limit the scope of the invention, one particular problem that arises when amplification enzymes are contaminated relates to the detection of bacterial sepsis in blood. PCR has been used to detect and diagnose bacterial sepsis. Rotbart, H. A., "Diagnosis of Enteroviral Meningitis with the Polymerase Chain Reaction," J. Pediatr. 117:85 (1990). Future opportunities are expected in rapid detection and identification of bacterial causes of sepsis and meningitis. White, T. J., et al., "The Polymerase Chain Reaction: Clinical Applications," Advances in Clin. Chem. 29:161 (1992). Universal primers have been described that are conserved in all eubacteria tested. This is also the case for fungi and enteroviruses. White, T. J., et al., supra. Primers which will act on any bacterial nucleic acid are useful in detecting sepsis because they ensure amplification of any possible bacterial nucleic acid present in the blood tested.

A diagram of the general procedure for detecting bacterial sepsis appears in FIG. 1. First, suitably prepared blood, (FIG. 1, "sample nucleic acid target"), is combined with PCR reagents, including universal primer and Taq polymerase, in a reaction vessel. Next, preferred amplification conditions are provided. Finally, the product is analyzed for the presence of amplified bacterial nucleic acid by polyacrylamide gel electrophoresis followed by autoradiography. The difficulty arises when the Taq polymerase introduced into the sample before PCR contains contaminating nucleic acid (FIG. 1, "Taq with Contaminating Bacterial Sequences"). If the contamination is of bacterial origin, possibly as a result of incomplete purification after production of commercial enzyme, this contaminating nucleic acid will also be amplified by the universal primers. This will lead to extra bands in the gel ("background noise") and false positive tests for bacterial sepsis.

The present invention contemplates methods for treating amplification enzymes such that any contaminating nucleic acid can not act as a template for amplification, or, in other words, is rendered unamplifiable. These methods are preferable to purification because they will inactivate substantially all of the contaminating nucleic acid treated, that is to say, the method approaches 100% effectiveness. In particular, these methods may be used for treating Taq polymerase to be used in PCR so that any nucleic acid is subsequently unamplifiable and will not result in undesired products of PCR (FIG. 2).

For example, addressing the problem of detecting bacterial sepsis, discussed above, the present invention contemplates treating Taq with photoreactive sterilization compound and irradiating to sterilize all contaminating nucleic acid sequences before adding Taq to the reaction vessel (FIG. 2). Then adding Taq to the blood/reagent mixture and proceeding with PCR amplification and amplicon detection. No Taq contaminating nucleic acid will be amplified in PCR because it will have been inactivated prior to the amplification, solving the problem of background noise and false positives.

Methods which are useful to achieve efficient nucleic acid sterilization have been identified and described in detail in U.S. Pat. No. 5,319,940 and U.S. patent applications Ser. Nos. 07/428,510 and 07/428,494. The entire contents of each are hereby incorporated by this reference.

DETAILED DESCRIPTION OF THE EMBODIMENTS

Figure 1:
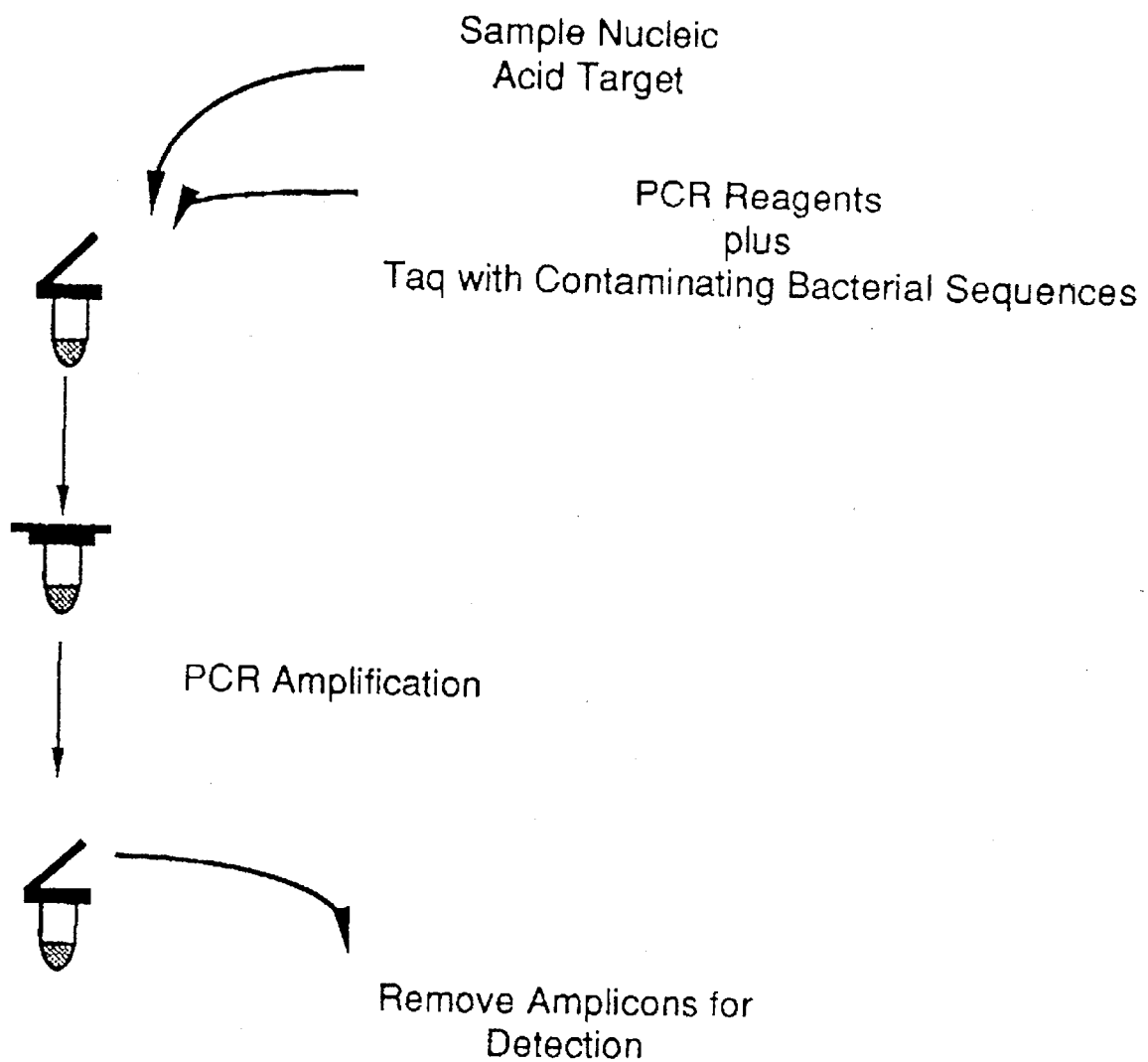
FIG. 1 shows schematically a manner of amplifying the impurities in potymerase.
Figure 2:
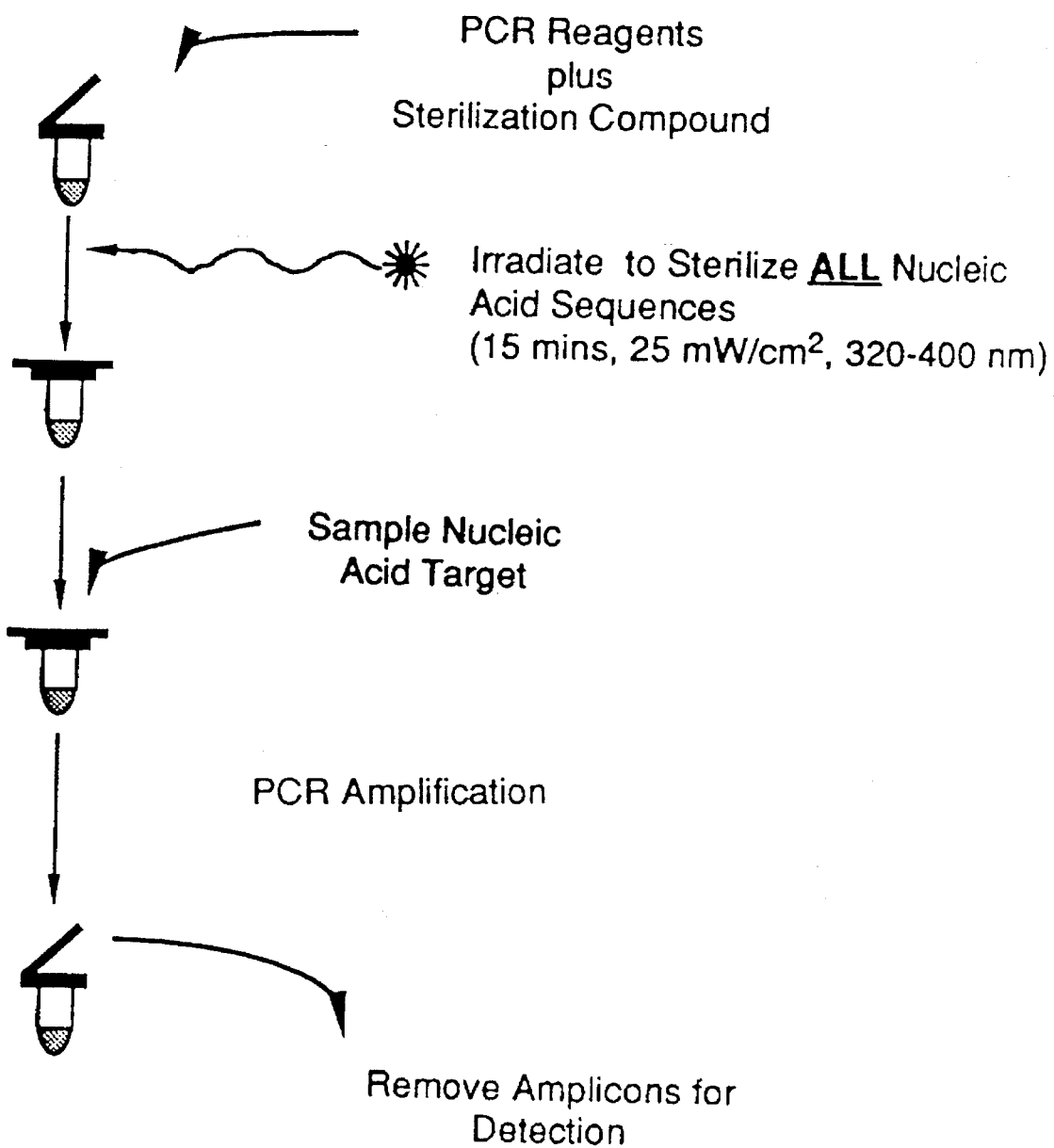
FIG. 2 shows schematically a manner of treating contaminated polymerase before using it to amplify nucleic acid target.

The PCR amplification method has many uses. It allows for production of large quantities of target nucleic acid fragments in a short period of time. PCR techniques can also be used to detect some genetic diseases because they include specific deletions and/or mutations in genomic DNA. These diseases may be detected by amplifying the target sequence and analyzing it by an appropriate method. In addition, various infectious diseases can be diagnosed by the presence in clinical samples of specific DNA sequences characteristic of the causative microorganism. Further, PCR techniques may greatly improve the specificity and sensitivity of already existing diagnostic procedures. However, where there is contaminating nucleic acid in the amplification enzyme essential to PCR, these valuable techniques will be less effective or not effective at all.

Where amplification enzymes are used in amplification protocols, it is desired that enzyme sterilization be essentially complete. Partial sterilization would leave some portion of the contaminating nucleic acid available for amplification, resulting in undesired product (depending on the sensitivity of the detection step).

The present invention generally relates to methods for rendering nucleic acid in enzyme preparations substantially unamplifiable, and in particular to methods for rendering DNA in Taq polymerase unamplifiable before the Taq polymerase is used in PCR.

Table 1 shows the ideal results. Where Taq polymerase contains target DNA ("pre") it can be exposed to an activation compound and UV light. Controls are also shown where contaminated Taq is not exposed to UV light. The experimental sample, and each control sample, is then processed using PCR to amplify any amplifiable nucleic acid. "Residual activity" is a measure of the percent of total nucleic acid introduced into the Taq sample which is amplified in the PCR.

Sample C, the sample of enzyme that contains contaminating nucleic acid and then treated with irradiation (ultraviolet), will ideally have no product of PCR because all the nucleic acid would be inactivated before PCR takes place. Of the controls, sample A will have 100% amplification because without UV exposure, the activation compound would not be activated and no inactivation of nucleic acid should occur. Samples B and D will have 100% amplification because target is added after the inactivation process occurs, and remains available for amplification.

TABLE 1

| Sample Activity | Compound | Target | | UV | Residual |
|---|---|---|---|---|---|
| | | pre | post | | |
| A | no | yes | no | no | 100 |
| B | yes | no | yes | no | 100 |
| C | yes | yes | no | yes | 0 |
| D | yes | no | yes | yes | 100 |

In application, the results may vary slightly due to lowered effectiveness of Taq polymerase as a result of the experimental conditions. In one embodiment, oxygen is removed from the sample ("degassing") prior to irradiation. Without wishing to be bound to any theory by which degassing improves Taq activity, it is expected that oxygen is converted into singlet oxygen during radiation with UV, which can damage the Taq polymerase. By degassing before irradiation, oxygen is not present to convert to singlet oxygen and damage the enzyme.

"Contaminating nucleic acid" is defined here as nucleic acid which is not sought to be amplified. "Amplifiable contaminating nucleic acid" is defined here as nucleic acid which is not sought to be amplified, yet is amplifiable.

"Amplification enzymes" are defined as enzymes that are used in an amplification protocol. For example, Taq polymerase is an amplification enzyme used in PCR amplification.

A protein preparation is defined as a mixture containing protein which is prepared for laboratory use. An enzyme preparation is similarly defined as a mixture containing one or more enzymes which is prepared for laboratory use.

Target sequences are "targets" in the sense that they are sought to be sorted out from other nucleic acid. Amplification techniques have been designed primarily for this sorting out. "Amplification" is a special case of replication involving template specificity. It is to be contrasted with nonspecific template replication (i.e. replication that is template-dependent but not dependent on a specific template). Template specificity is here distinguished from fidelity of replication (i.e. synthesis of the proper polynucleotide sequence) and nucleotide specificity (ribo- or deoxyribo-).

Photoreactive Compounds

"Activation compounds" defines a family of compounds that undergo chemical change in response to triggering stimuli. Triggering stimuli include, but are not limited to, thermal stimuli, chemical stimuli and electromagnetic stimuli. "Activating" an activation compound is defined as exposing the compound to stimuli capable of triggering a chemical change in the activation compound. As disclosed in U.S. Pat. No. 5,319,940 (hereby incorporated by reference), "Photoreactive, activation compounds" (or simply "photoreactive compounds"), defines a genus of compounds in the activation compound family that undergo chemical change in response to electromagnetic radiation. Generally, such compounds are capable of forming covalent bonds with nucleic acids. Such photoreactive compounds include those identified in Table 2.

One genus of photoreactive compounds is commonly referred to as the furocoumarins. The furocoumarin derivatives belong to two

TABLE 2

| Photoreactive Compounds |
| --- |
| Actinomycins |
| Anthracyclinones |
| Anthramycin |
| Benzodipyrones |
| Fluorenes and fluorenones |
| Furocoumarins |
| Mitomycin |
| Monostral Fast Blue |
| Norphillin A |
| Organic dyes |
| Phenanthridines |
| Phenazathionium Salts |
| Phenazines |
| Phenothiazines |
| Phenylazides |
| Polycyclic hydrocarbons |
| Quinolines |
| Thiaxanthenones | main categories: 1) psoralens [7H-furo(3,2-g)-(1)-benzopyran-7-one, or δ-lactone of 6-hydroxy-5-benzofuranacrylic acid], which are linear and in which the two oxygen residues appended to the central aromatic moiety have a 1, 3 orientation, and further in which the furan ring moiety is linked to the 6 position of the two ring coumarin system, and 2) the isopsoralens [2H-furo(2,3 -h)-(1)-benzopyran-2-one, or δ-lactone of 4-hydroxy-5-benzofuranacrylic acid], which are angular, in which the two oxygen residues appended to the central aromatic moiety have a 1, 3 orientation, and further in which the furan ring moiety is linked to the 8 position of the two ring coumarin system. Psoralen derivatives are derived from substitution of the linear furocoumarin at the 3, 4, 5, 8, 4', or 5' positions, while isopsoralen derivatives are derived from substitution of the angular furocoumarin at the 3, 4, 5, 6, 4', or 5 positions.

Sterilization

A. Sterilization In General

Something is "sterilized" when it is rendered incapable of replication. While the term "sterilization" has typically been applied only in the context of living organisms, it is here meant to be applied to in vitro amplification protocols of polynucleotides where a template polynucleotide functions in the nature of a germination seed for its further propagation.

Sterilization "sensitivity" is an operationally defined term. It is defined only in the context of a "sterilization method" and the particular detection method that is used to measure templates (or organisms). Sterilization sensitivity is the number of germination seeds (e.g., viable bacterial cells or polynucleotide templates) that result in a measurable signal in some sterilization method and defined detection assay.

To appreciate that a "sterilization method" may or may not achieve "sterilization," it is useful to consider a specific example. A bacterial culture is said to be sterilized if an aliquot of the culture, when transferred to a fresh culture plate and permitted to grow, is undetectable after a certain time period. The time period and the growth conditions (e.g. temperature) define an "amplification factor". This amplification factor along with the limitations of the detection method (e.g. visual inspection of the culture plate for the appearance of a bacterial colony) define the sensitivity of the sterilization method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the "sterilization method" appears to be completely effective (and above which "sterilization" is, in fact, only partially effective). This interplay between the amplification factor of an assay and the threshold that the detection method defines, can be illustrated. Referring now to Table 3 bacterial cells are applied to a plate under two different sets of conditions: in one case, the growth conditions and time are such that an overall amplification of $10^4$ has occurred; in the other case, the growth conditions and time are such that an overall amplification of $10^8$ has occurred. The detection method is arbitrarily chosen to be visual inspection. The detectable

TABLE 3

| AMPLIFICATION FACTOR | # OF VIABLE BACTERIAL CELLS APPLIED TO A PLATE | | | | |
| --- | --- | --- | --- | --- | --- |
| | 1 | 10 | 100 | 1000 | |
| $10^4$ | $10^4$ | $10^5$ | $10^6$ | $10^7$ | # of Bacterial cells after Amplification |
| | − | − | + | ++ | Detection (+/−) |
| $10^8$ | $10^8$ | $10^9$ | $10^{10}$ | $11^{11}$ | # of Bacterial cells after Amplification |
| | ++ | +++ | +++ | ++++ | Detection (+/−) | signal will be proportional to the number of bacterial cells actually present after amplification. For calculation purposes, the detection threshold is taken to be $10^6$ cells; if fewer than $10^6$ cells are present after amplification, no cell colonies are visually detectable and the sterilization method will appear effective. Given the amplification factor of $10^4$ and a detection threshold of $10_6$, the sterilization sensitivity limit would be 100 bacterial cells; if less than 100 viable bacterial cells were present in the original aliquot of the bacterial culture after the sterilization method is performed, the culture would still appear to be sterilized. Alternatively, if the time and growth conditions permitted an amplification of $10^8$, then the sterilization sensitivity limit (assuming the same detection threshold) would be 1 bacterial cell. Under the latter conditions, the sterilization method must be sufficiently stringent that all bacterial cells are, in fact, incapable of replication for sterilization to appear complete (i.e. the sterilization method would need to cause sterilization, not just substantial sterilization).

B. Sterilization of Potential Contamination

The same considerations of detection threshold and amplification factor are present when determining the sensitivity limit of a sterilization method for nucleic acid. Again, by "sterilization" it is meant that the nucleic acid is rendered incapable of replication; or unamplifiable.

The sterilization method of the present invention renders nucleic acid substantially unamplifiable. In one embodiment, the sterilization method renders nucleic acid in amplification enzyme preparations unamplifiable. Also, in one embodiment, the sterilization method of the present invention renders DNA in Taq preparations substantially unamplifiable.

It is not intended that the sterilization method of the present invention be limited by the nature of the nucleic acid; it is contemplated that the sterilization method render all forms of nucleic acid (whether DNA, mRNA, etc.) substantially unamplifiable.

"Template" encompasses both the situation where the nucleic acid contains one or more segments of one or more target sequences, and the situation where the nucleic acid contains no target sequence (and, therefore, no segments of target sequences). "Template" also encompasses both the situation where the nucleic acid contains one or more replicable probes, and the situation where the nucleic acid contains no replicable probes. Where template is used for amplification and amplification is carried out, there is "amplification product." Just as "template" encompasses the situation where no target or probe is present, "amplification product" encompasses the situation where no amplified target or probe is present.

While it is not intended that the present invention be limited to any theory by which nucleic acid is rendered substantially unamplifiable by the methods and compounds, it is expected that sterilization occurs by either 1) modification of nucleic acid, or 2) inhibition of the amplification enzyme itself. Again, while not limited to any mechanism, it is expected that, if modification of nucleic acid occurs with sterilizing compounds, it probably occurs because the compounds react with amplified nucleic acid to create sufficient adducts per base (i.e. sufficient "modification density") such that statistically all strands are prevented from either 1) subsequent use of the denatured nucleic acid in single stranded form as template for amplification or 2) dissociation of the double stranded form of the nucleic acid into single strands, thereby preventing it from acting as a template for subsequent amplification.

In the case of activation compounds modifying nucleic acid, it is preferred that interaction of the nucleic acid (whether DNA, mRNA, etc.) with the activation compound causes the amplification enzyme to differentiate between actual target sequences and contaminating nucleic acid, such that, should contaminating nucleic acid be introduced into an amplification, it will not be amplified.

EXPERIMENTAL

The following examples serve to illustrate certain preferred embodiments and aspects of the present invention and are not to be construed as limiting the scope thereof.

In the experimental disclosure which follows, the following abbreviations apply: M (Molar); μM (micromolar); mol (moles); mmol (millimoles); μmol (micromoles); nmol (nanomoles); pmol (picomoles); gm (grams); mg (milligrams); μg (micrograms); L (liters); ml (milliliters); μl (microliters); cm (centimeters); mm (millimeters); μm (micrometers); nm (nanometers); °C. (degrees Centigrade); Ci (Curies); uCi (microCuries); MW (molecular weight); OD (optical density); DMSO (dimethyl sulfoxide); EDTA (ethylenediamine-tetracetic acid); 1×Tm (buffer: 10 mM Tris/1 mM EDTA, pH 7.5); 1×Taq (buffer: 50 mM KCl, 2.5 mM $MgCl_2$, 10 mM Tris, pH 8.5, 200 μg/ml gelatin); PAGE (polyacrylamide gel electrophoresis); UV (ultraviolet); V (volts); W (watts); mW (milliWatts); mA (milliamps); bp (base pair); CPM (counts per minute).

In some of the examples below, 8-methoxypsoralen is used. Generally, stock 8-MOP is diluted in DMSO (100 mg/ml) and added to a final concentration of 300 μg/ml.

Where polyacrylamide gel electrophoresis (PAGE) is used, denaturing (7 or 8M urea) polyacrylamide gels (28 cm×35 cm×0.4 mm) were poured and pre-electrophoresed for 30 to 60 minutes at 2000 Volts, 50 Wats, 25 milliamps. 10 to 12.5% gels were used for oligonucleotides between 40 and 400 base pairs in length; 6 to 8% gels were used for longer sequences. Depending on the length of DNA to be analyzed, samples were loaded in either 8M urea, containing 0.025% tracking dyes (bromphenol blue and xylene cyanol), or in 80% formamide, 10% glycerol, 0.025% tracking dyes, then electrophoresed for 2–4 hours at 2000 Volts, 50 Watts, 25 milliamps. Following PAGE, individual bands were, in most cases, visualized by autoradiography. Autoradiography involved exposure overnight at −70° C. to Kodak XAR-5 films with an intensifying screen.

In order to visualize with autoradiography, PCR products were internally radiolabelled. This simply involved adding 2 µCi of α-$^{32}$P-dCTP (3000 Ci/mmole, NEN Research Products, Boston Mass., U.S.A.) to each PCR reaction. The internally-radiolabelled PCR products are directly fractionated by this denaturing PAGE.

In some cases, the visualized bands were cut from the gel and collected for scintillation counting. Scintillation counting involved the use of a scintillation fluid and a commercial scintillation counter (Searle Analytic 92, Model #000 006893).

Generally, PCR was carried out using 175–200 µM dNTPs (deoxyribonucleoside 5'-triphosphates) and 0.1 to 1.0 µM primers. 2.5 to 5.0 Units/100 µl of Taq polymerase was used. PCR reactions were overlaid with 30–100 µl light mineral oil. A typical PCR cycle for HIV amplification using a Perkin-Elmer Cetus DNA Thermal Cycler (Part No. N8010150) was: denaturation at 95° C. for 30 seconds; annealing at 55° C. for 30 seconds; and extension at 72° C. for 1 minute. PCR cycles were normally carried out in this manner for between 20 to 30 cycles followed by 7 minutes at 72° C. PCR product or "amplicon" was then detected.

In some cases, PCR was carried out on an HIV system. This system provides a 115-mer product designated HRI 46:

5'- AT AAT CCA CCT ATC CCA GTA GGA GAA ATT TAT AAA AGA TGG ATA ATC CTG GGA TTA AAT AA
AAT AGT AAG AAT GT ATA GCC CTA CCA GCA TTC TGG ACA TAA GAC AAG GAC CAA A -3' and its complement, designated HRI 47:

3'- TAT TAG GTG GAT AGG GTC ATC CTC TTT AAA TAT TTT CTA CCT ATT AGG ACC CTA ATT TAT T
TT ATC ATT CTT ACA TAT CGG GAT GGT CGT AAG ACC TGT ATT CTG TTC CTG GTT T-5'

These sequences were used by C. Y. Ou et al, Science 39:295 (1988).

Example 1

In this example, a sample of commercially prepared Taq polymerase was tested for contamination with amplifiable nucleic acid. A sample of Taq polymerase from Perkin Elmer Cetus Laboratories was processed using the PCR reaction to determine if any DNA would be replicated, which would suggest DNA contamination of the enzyme.

As a control, E. coli was prepared by placing an E. coli colony in 40 ul of protease K (15 ul B', 25 ul B2, 10 ul E. Coli stock). This mixture was heated at 55 C for 30', then 95 C for 5'.

PCR reagents and Taq polymerase were added to 50 ul water, or, as controls, 40 ul water and 10 ul E. coli stock (undiluted, at a 1:10 dilution, and at a 1:100 dilution). The PCR reagents were present in the following final concentrations: 10 mM Tris pH 8.3, 50 mM KCl, 2 mM MgCl$_2$, 0.25 mM total dNTP, 0.5 uM each primers HRI 100 and HRI 200, 2% glycerol, and 2.5 units of Taq polymerase. The PCR reaction was run for 5' at 95 C, 50 cycles of 25" at 95 C followed by 25" at 50 C, then 10' at 72 C. The PCR products were analyzed by electrophoresis on a 2% Nusieve /0.5% Seakem agarose gel followed by ethidium bromide staining and visualization on a UV transilluminator.

In the results (not shown) PCR product was detected in two of the four Taq polymerase samples. The PCR product in the Taq lanes of this gel were very similar to the migration observed with E. coli template; the bands are of unknown origin and were not expected in this experiment. The results indicate that contaminating nucleic acid in Taq polymerase preparations will clutter and confuse experimental results. Such cluttering of the experiment with contaminating DNA is likely to create false positive results.

Example 2

Figure 3:
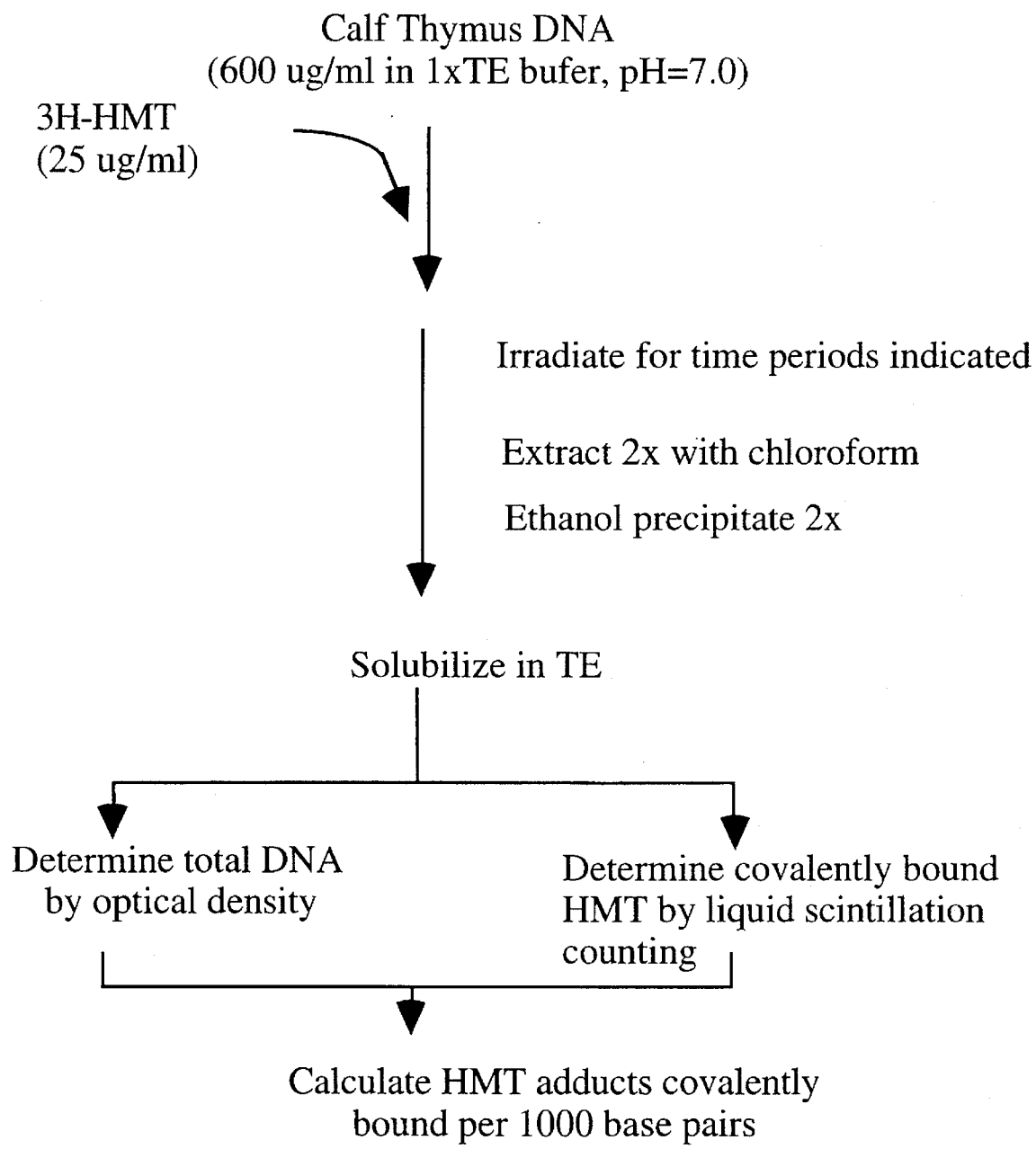
FIG. 3 is a flow chart schematically showing a manner of measuring the binding of photoreactive compounds to nucleic acid.

This example investigates the ability of psoralens to bind nucleic acid. Tritiated 4'-hydroxymethyl-4,5',8-trimethylpsoralen ($^3$H-HMT) was used to measure psoralen binding to calf thymus DNA. The procedure was as shown in FIG. 3. $^3$H-HMT was mixed with the DNA and irradiated using the HRI 100 photoactivation device (HRI Research, Concord, Calif.). The product was then extracted with chloroform to separate the unbound $^3$H-HMT. The nucleic acid was then precipitated and solubilized. Bound HMT was determined by scintillation counting along with measuring the optical density of the DNA solution.

The results (not shown) revealed that plateau binding of 52 crosslinks per 1000 b.p. was reached in less than five minutes. Plateau binding might be reached more quickly by the use of a polycarbonate tube.

Example 3

This example investigates the ability of isopsoralens to bind to DNA. It will be desirable in some situations to have precise control of the binding levels of a photoactive compound to nucleic acids. Thus, this example further explores how the concentration of the photoactive compound affects the ultimate binding levels. In this example, an isopsoralen, 4'-Aminomethyl- 4,5'-dimethylisopsoralen (AMDMIP), is analyzed for levels of binding to nucleic acid as a function of concentration. Following the procedure outlined in FIG. 3, $^3$H-AMDMIP was used at different concentrations to measure binding to calf thymus DNA. Samples of 25 ug/ml of $^3$H-AMDMIP were added to 600 ug/ml Calf Thymus DNA suspended in 1×TE buffer at pH 7.0. The samples were then irradiated for 30", chloroform extracted twice, Ethanol precipitated twice, and resuspended in TE buffer. The total DNA was determined by optical density. Total AMDMIP adducts were determined by liquid scintillation counting.

Figure 4:
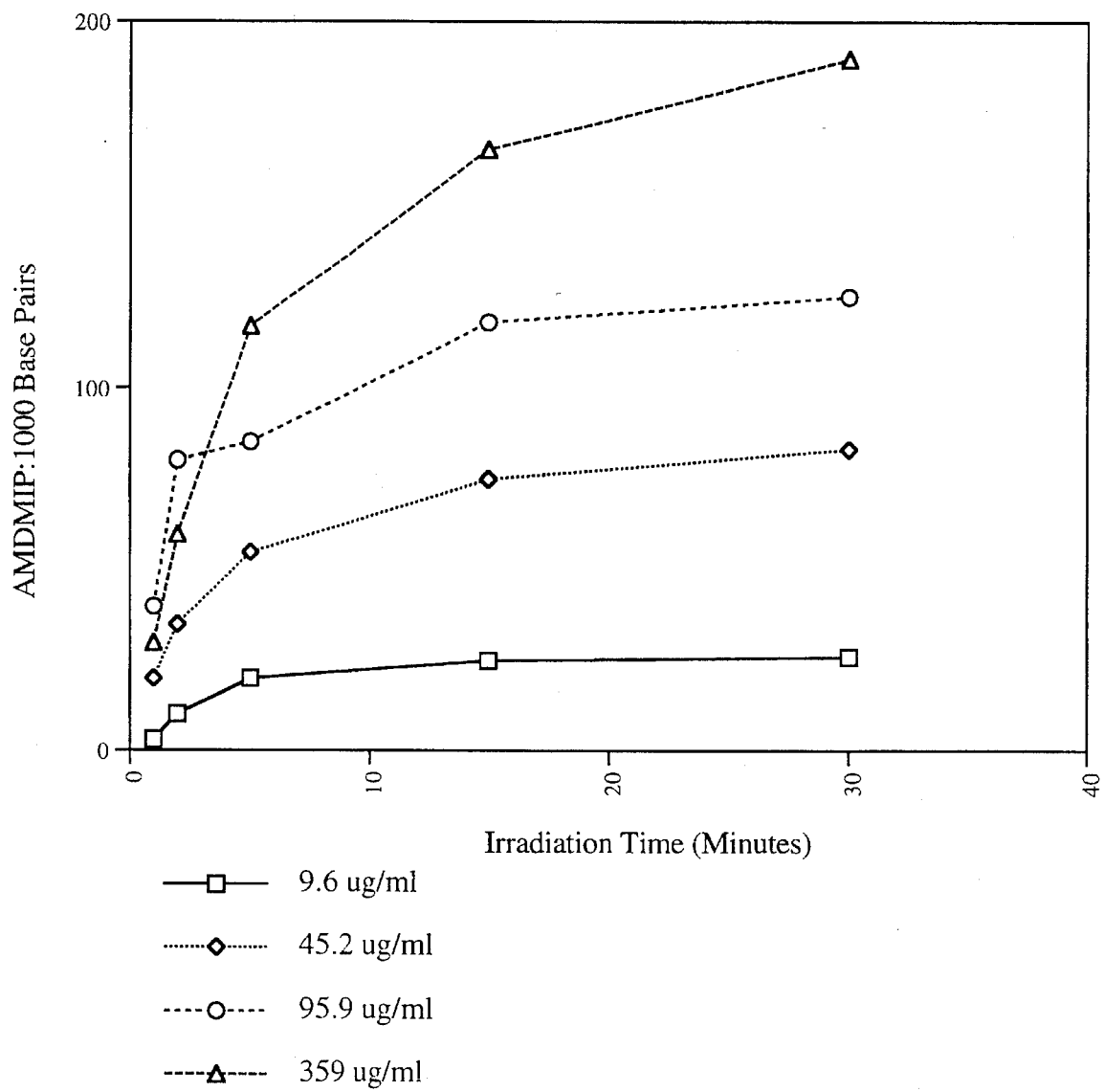
FIG. 4 shows binding as a function of concentration and irradiation time.

The results are shown in FIG. 4. The results show that at a concentration of 359 ug/ml AMDMIP, binding after 30' irradiation was 195 crosslinks per 1000 b.p. Yet at a concentration of 9.6 ug/ml, binding was only 25 crosslinks per 1000 b.p. Clearly, the concentration of AMDMIP affects the binding levels achieved with calf thymus DNA. Providing irradiations are of sufficient duration to achieve plateau levels, the concentration dependence can be used to precisely control addition reactions so that only the concentration of sterilizing compound required need be used. The results also support the practice of using surplus sterilizing compound to ensure that maximum binding is achieved.

Example 4

This example shows that isopsoralens block amplification of nucleic acid in a length dependant fashion. It is expected that sensitivity of sterilization will depend upon both the modification density and the length of the PCR target sequences. In this experiment, the effect of modification density and target length on sterilization sensitivity were examined by sterilizing two different length PCR products with AMDMIP. The isopsoralen was used at two different concentrations for the sterilization procedure to produce differing modification densities on PCR targets.

The two PCR targets used in these experiments were a 115-mer (SK-38/SK-39 HIV system) and a 500-mer. The 500-mer target is obtained from a PCR amplification of a lambda plasmid with primers PCR 01/02. This system is provided by Cetus/Perkins Elmer as a control in their commercial kits of PCR reagents (Catalogue No. N801-0055). For both of these systems equivalent copy numbers of each target were prepared in the following manner: An initial 30 cycle PCR reaction was carried out for each system with the appropriate primers and targets. Aliquots (approximately $10^5$–$10^6$ target copies) of each of these reactions were transferred to a second set of PCR reactions. These second sets of PCR amplifications were carried out in the presence of a $\alpha$-$^{32}$P-dCTP, again for 30 cycles. Aliquots of these reactions were removed and counted by liquid scintillation counting. With these numbers, the specific activity of the $\alpha$-$^{32}$P-dCTP, and the sequence of each of the PCR product oligonucleotides (115-mer and 500-mer), the concentrations of each of the two PCR product oligonucleotides in the second set of PCR reaction tubes was determined. Both the 115-mer and the 500-mer concentrations were then adjusted to exactly $1 \times 10^{-8}$M by the addition of additional Taq buffer. These stocks of equivalent copy number of PCR products were then used for further investigation. Each of the stock solutions then was split into two reaction tubes. The reaction tubes were adjusted to contain the following: Tube 1, 100 ug/ml AMDMIP; and Tube 2, 400 ug/ml AMDMIP. Each of these samples were again split into two portions, one part being irradiated for 15 minutes at room temperature with the HRI-100 device and the other part kept in the dark. Serial dilutions of the irradiated and the non-irradiated targets were then carried out on these samples for 30 cycles in the presence of $\alpha$-$^{32}$P-dCTP. aliquots of these samples were analyzed on denaturing polyacrylamide gels. The PCR product bands were visualized by autoradiography, cut, and counted in a liquid scintillation counter.

Figure 5:
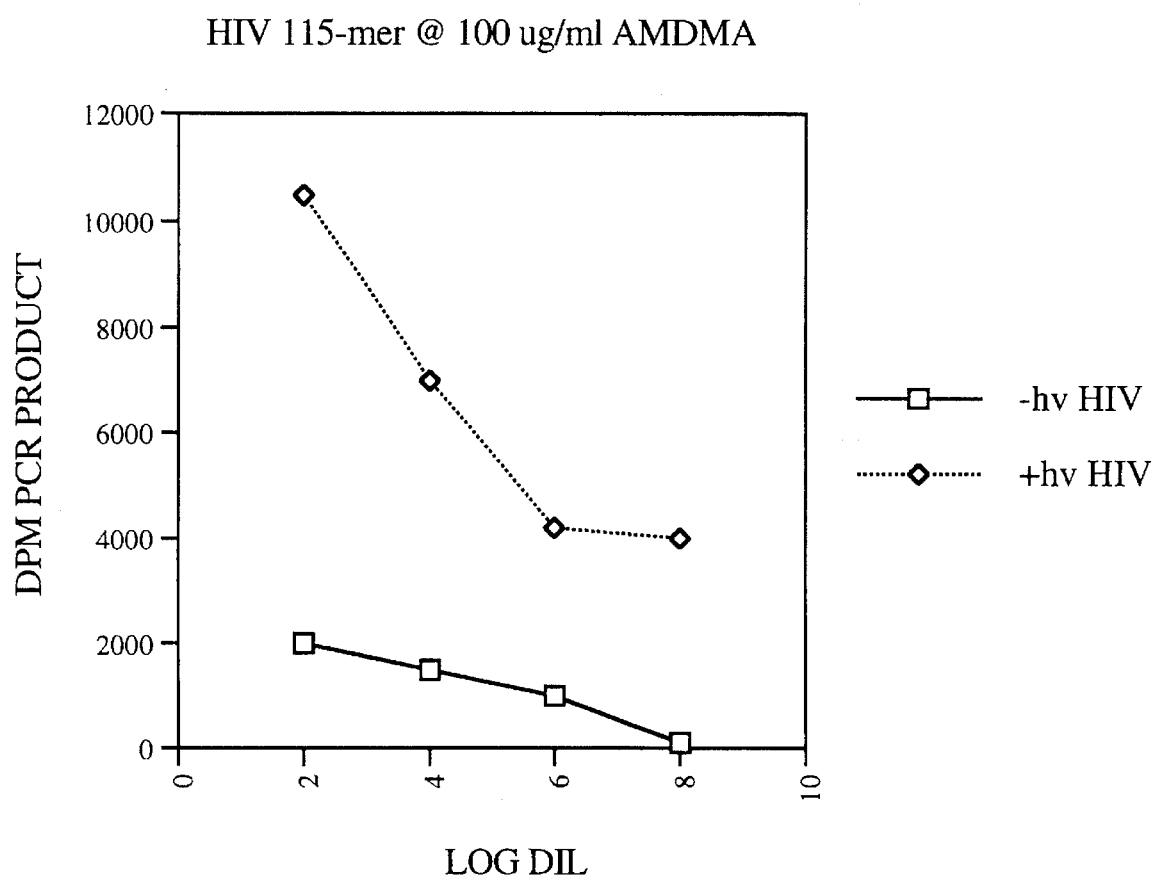
FIG. 5 shows plotted counts of PCR product bands that were visualized by autoradiography, cut and counted in a liquid scintillation counter.

FIG. 5 shows that AMDMIP at 100 ug/ml achieves substantial sterilization of the 115-mer PCR product. When AMDMIP was used at 400 ug/ml, the irradiated carryover series yielded no signal at all up to $6 \times 10^9$ molecules of carryover with the 115-mer PCR product (not shown). The non-irradiated controls yield normal levels of PCR signals from the carryover molecules. When AMDMIP was used with the 500-mer PCR product (not shown), both 100 ug/ml and 400 ug/ml concentrations resulted in no signal in the irradiated dilution series. AMDMIP at 100 ug/ml has a high enough modification density on the 500-mev target that there appears to be no non-sterilized 500-mers in $6 \times 10^9$ carryover molecules with the $\alpha$-$^{32}$P assay for PCR product.

Example 5

Figure 6:
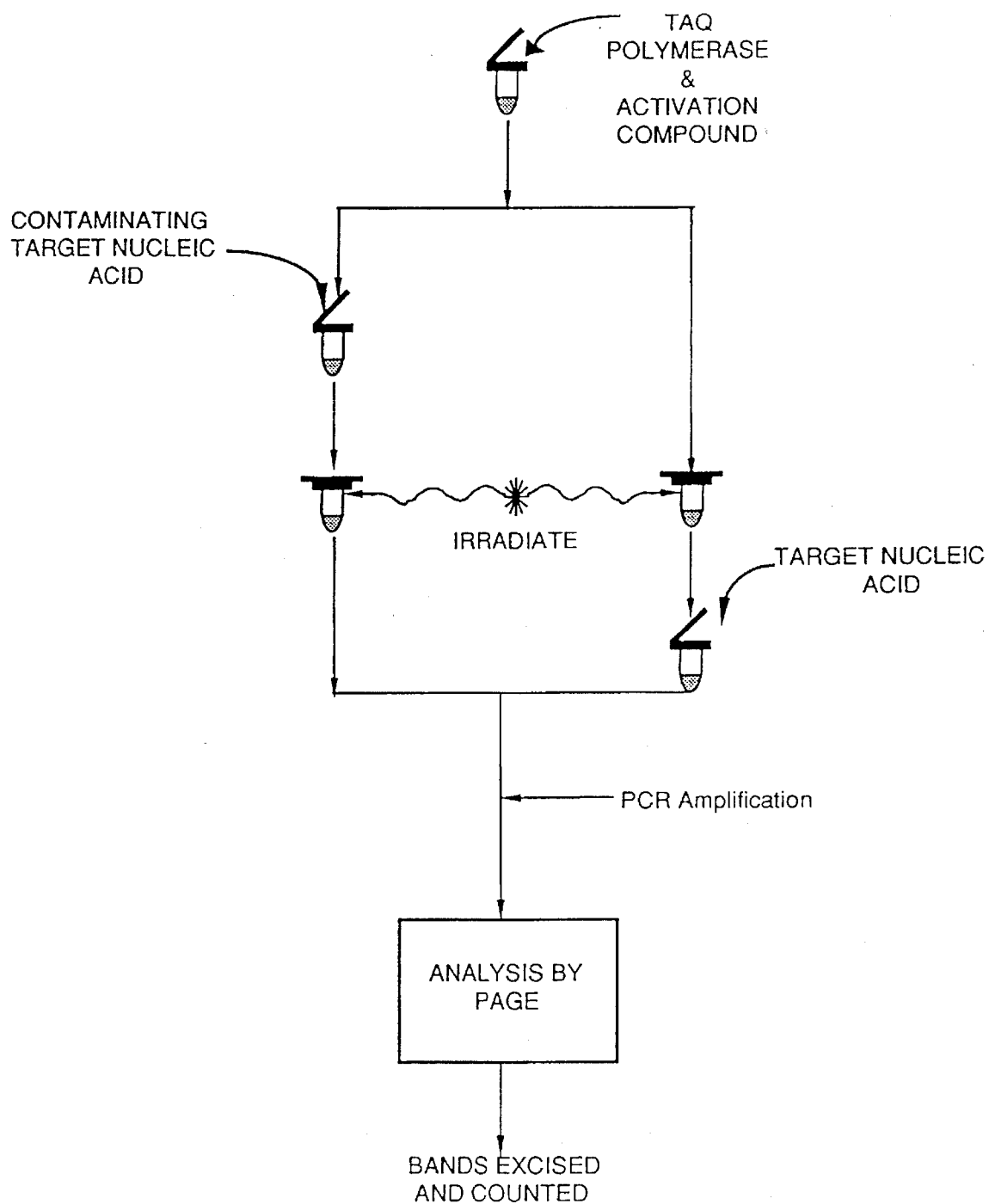
FIG. 6 shows schematically a manner of measuring the extent to which contamination nucleic acid is rendered unamplifiable in Taq polymerase by an embodiment of this invention.
Figure 7:
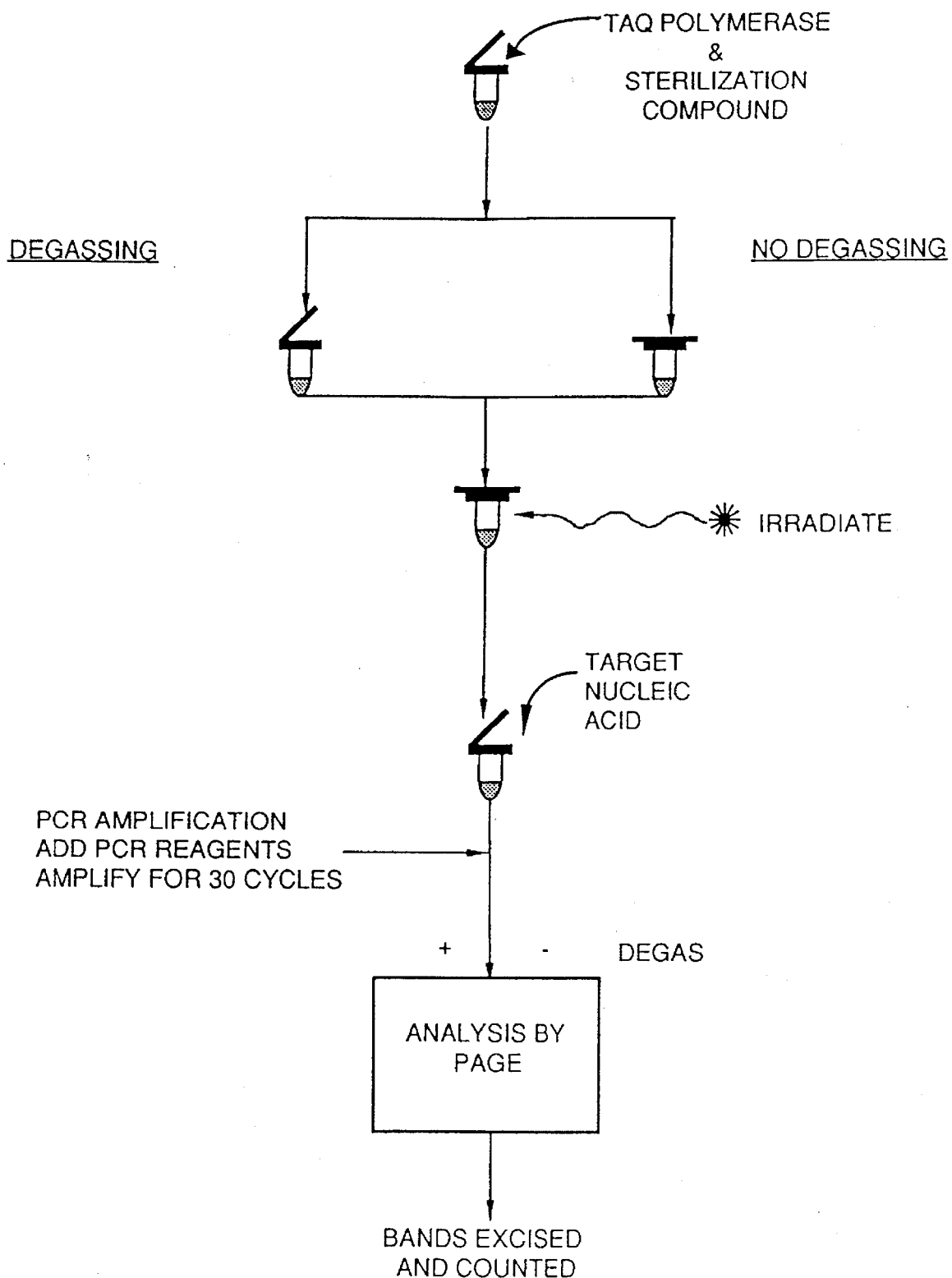
FIG. 7 shows schematically a manner of measuring the effects of degassing on Taq polymerase activity.

The following example was carried out as shown in FIG. 6 and FIG. 7. FIG. 6 shows schematically a manner of measuring the sterilization of contamination nucleic acid in Taq polymerase by an embodiment of this invention. Two Taq samples were prepared and treated with activation compound. One sample was seeded with contaminating target nucleic acid, then irradiated to activate the compound, and finally processed using PCR. The other sample was treated similarly, but not seeded until after irradiation. By comparing the PCR products from Taq contaminated with target nucleic acid before versus Taq with target nucleic acid added after the sterilization procedure, it is possible to detect any sterilization of the contaminating target nucleic acid.

FIG. 7 shows schematically a manner of measuring the effects of degassing (removing oxygen) on Taq polymerase activity. Without intending to limit the scope of the invention, it is expected that oxygen is converted into singlet oxygen during radiation with UV, which can damage the Taq polymerase. By degassing before irradiation, oxygen is not present to convert to singlet oxygen and damage Taq. In FIG. 7, two samples of Taq were seeded with mock target after Taq was treated with an activation compound and UV light. Oxygen was removed from one sample prior to irradiation. The other sample was not degassed. By carrying out PCR and comparing the PCR products from each sample, we can determine whether degassing protects Taq activity during irradiation.

In accordance with FIG. 6 and FIG. 7, the following specific steps were taken to perform the experiment. As starting material, each sample contained 35 ul Taq polymerase enzyme diluted in 1.43×Taq buffer to 0.5 ul/35 ul, or 2.5 units. Mock target of 2.5×10(6) copies in 1.25 ul was added either before or after sterilization. The mock target was a 115-mer (SK-38/SK-39 HIV system). To the samples receiving activation compound, 5 ug of 4'-aminomethyl-4, 5',8-trimethylpsoralen (AMT) in 5 ul was added. Water was then added to each sample to 45 ul. The samples to be degassed were then treated as follows: 1) freeze sample in dry ice/ethanol, 2) thaw and apply vacuum for 30",3) repeat 2 times. The samples to be irradiated were tightly capped, placed on the HRI-100 irradiation device (described above) and irradiated with UV for 5' at room temperature. The samples were then prepared for PCR with the addition of primers, dNTP's and target where indicated. Each PCR contained in 50 ul: 1 uM each of dATP, dCTP, dGTP and dTTP, 188 uM dNTP, 10 µCi of $^{32}$P-dCTP, 50 mM KCl 2.5 mM MgCl2, 0.02% gelatin, 50 pmol of the upstream primer GH26, and 50 pmoles of the downstream primer GH27. All samples were then exposed to PCR conditions as follows: 30 cycles of 92 C for 1',55 C for 2',72 C for 1'. The amplified products were analyzed by polyacrylamide gel electrophoresis and visualized by autoradiography (Table 4). The bands were cut from the gel and collected for scintillation counting on a commercial scintillation counter.

TABLE 4

Comparison of the Relative PCR Amplification Signal of AMT Treated, Taq Polymerase with Untreated Control.

| Sample | Compound | Target pre | Target post | Degassing | UV | Residual Enzyme Activity |
|---|---|---|---|---|---|---|
| A | yes | yes | no | no | no | 100 |
| B | yes | no | yes | yes | no | 98 |
| C | yes | yes | no | yes | yes | 19 |
| D | yes | no | yes | no | yes | 35 |
| E | yes | no | yes | yes | yes | 56 |

This experiment shows that the present invention results in sterilization of contaminating DNA in commercial preparations of Taq polymerase. Following the steps of the schematic diagram shown in FIG. 6 and explained above, the results were as follows: Taq with contaminating target which was exposed to sterilization (Table 4, sample C) showed only 19% residual activity. In contrast, Taq with target introduced after the sterilization process (Table 4, sample E) showed 56% residual activity.

The results of this experiment further suggest Taq activity may be effected by changes in oxygen due to irradiation. Taq seeded with mock target which is treated with activation compound without UV is considered to have 100% activity (Table 4, sample A). Taq which is treated similarly, but is treated with the degassing procedure has only a 2% drop in activity (Table 4, sample B). In comparison, Taq which is treated with both activation compound and UV has a 65% drop in activity (Table 4, sample D). The results further indicate that it is possible to control this damage of Taq by degassing (removing oxygen from the sample) prior to irradiation.

Degassing before irradiation is shown to preserve Taq polymerase activity. Following the steps of the schematic diagram shown in FIG. 7 and described above, the results were as follows: the residual activity of the degassed sample (Table 4, sample E) was 21% higher than the untreated sample (Table 4, sample D).

Example 6

In this experiment, sterilization of another protein is studied. As starting material, $0.8 \times 10^8$ lymphocytes were seeded into 10 ml of clotting Factor VIII concentrate. 8-MOP was added to a final concentration of 300 ug/ml. $^3$H-8-MOP was added to a specific activity of 4.73 uCi/mg. The Factor VIII concentrate was irradiated in a petri dish. The sample was irradiated from above and below by GE type F20T12-BLB fluorescent UVA (320–400 nm) bulbs with an electric fan blowing gently across the lights to cool the area. The temperature was maintained between 22° and 27° C. during irradiation. Available UVA light was measured (by a Black-ray long wave UV meter) with both light banks turned on. The total measured light intensity was 3.5–4.8 mW/cm$^2$. The Factor VIII concentrate irradiation was carried out with no $O_2$ control. Control samples included one which received no treatment and one to which only 8-MOP was added and no UVA light was applied.

Figure 8:
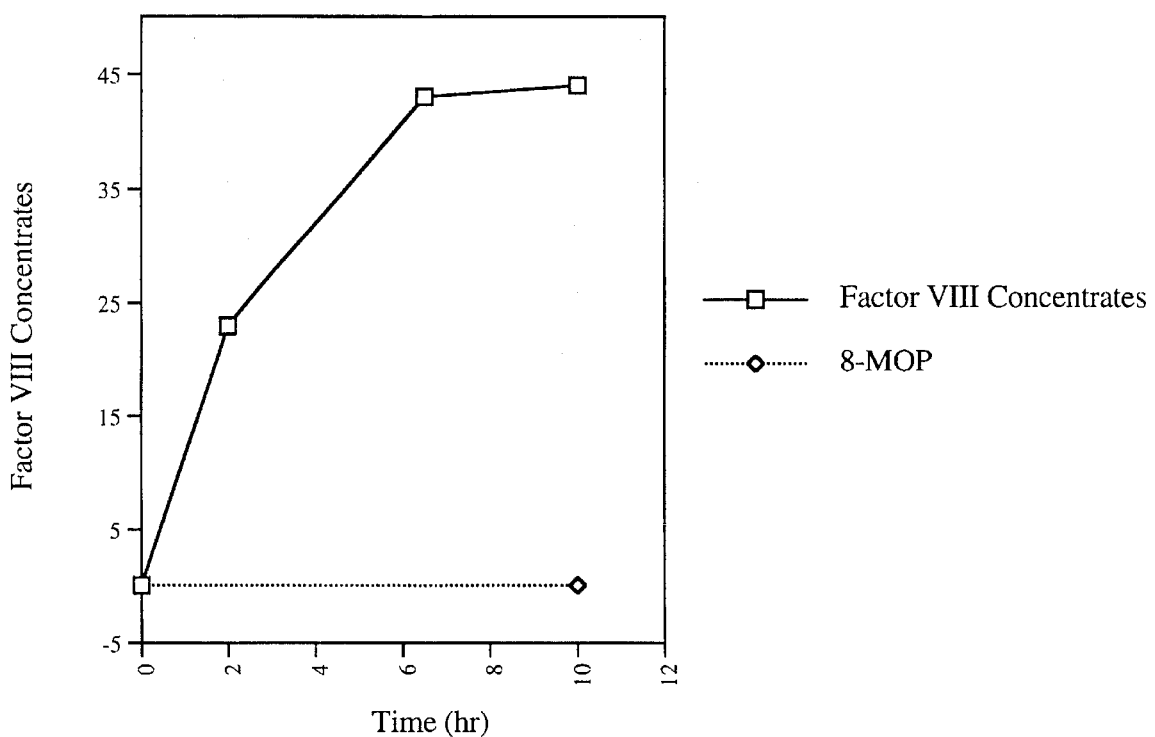
FIG. 8 is a graph showing the photoaddition of 8-methoxypsoralen to contaminating nucleic acid in Factor VIII.

Following irradiation, total cellular lymphocyte DNA was extracted by phenol extraction following proteinase K digestion. The DNA was then ethanol precipitated three times. The number of 8-MOP molecules covalently bound per 1,000 base pair was determined by measuring the quantity of DNA ($A_{260}$ nm) using a spectrophotometer and the $^3$H-CPM associated with the DNA using a scintillation counter. FIG. 8 shows that 8-MOP adduct formation is a function of UVA irradiation time. Treatment with 8-MOP alone without UVA light for up to 10 hours resulted in no 8-MOP addition to cellular DNA. For Factor VIII concentrates, 8-MOP adducts reached a level of 43.5/1,000 bp after 6 hours of UVA irradiation. Most importantly, at this level of sterilization, Factor VIII was still active (data not shown).

We claim:

1. A method for rendering nucleic acid in *Thermus aquaticus* polymerase preparations unamplifable, comprising, in the order named:

a) providing in any order, as reaction components:
      i) a *Thermus aquaticus* polymerase preparation suspected of containing amplifiable contaminating bacterial nucleic acid,
      ii) a furocoumarin;

b) adding in any order
      i) said *Thermus aquaticus* polymerase preparation, and
      ii) said furocoumarin;
   to make a reaction mixture;

c) removing oxygen gas from said reaction mixture; and d) activating said furocoumarin with ultraviolet irradiation to create a treated *Thermus aquaticus* polymerase preparation such that said amplifiable contaminating nucleic acid is rendered unamplifiable; and e) utilizing said treated *Thermus aquaticus* polymerase preparation with primers in cycles of amplification to increase the concentration of a desired amplified segment of a target sequence so that it becomes the predominant sequence in a mixture of nucleic acids.

2. The method of claim 1, wherein said amplifiable containing nucleic acid is deoxyribonucleic acid.

3. The method of claim 1, wherein said furocoumarin is a psoralen.

4. The method of claim 1, wherein said furocoumarin is a isopsoralen.

5. The method of claim 1, wherein said furocoumarin is 8-methoxypsoralen.

6. The method of claim 1, wherein said furocoumarin is 4'-hydroxymethyl-4,5',8-trimethylpsoralen.

7. The method of claim 1, wherein said furocoumarin is 4'-aminomethyl-4,5'-dimethylisopsoralen.

* * * * *